United States Patent [19]

Bruza et al.

[11] Patent Number: 5,274,135

[45] Date of Patent: Dec. 28, 1993

[54] PROCESS FOR PREPARING AMINOBENZOCYCLOBUTENES

[75] Inventors: Kenneth J. Bruza, Alma; Arnold E. Young, Midland; Kurt A. Bell, Coleman, all of Mich.

[73] Assignee: The Dow Chemical Company, Midland, Mich.

[21] Appl. No.: 763,016

[22] Filed: Sep. 20, 1991

[51] Int. Cl.$^5$ .................. C07C 209/10; C07C 209/18; C07C 209/48

[52] U.S. Cl. ............................ 548/476; 548/474; 548/529; 548/549; 564/393; 564/395; 564/405; 564/407; 564/413; 564/428

[58] Field of Search .............. 564/405, 407, 393, 395, 564/413, 428; 548/474, 476, 529, 549

[56] References Cited

U.S. PATENT DOCUMENTS

| | | | |
|---|---|---|---|
| Re. 17,280 | 4/1929 | Hale et al. | 564/407 |
| 3,256,329 | 6/1966 | Kauer | 564/407 |
| 3,865,876 | 2/1975 | Chenevey et al. | 564/407 |
| 4,380,670 | 4/1983 | Nishiyama et al. | 564/407 |
| 4,540,763 | 9/1985 | Kirchhoff et al. | 526/281 |
| 4,544,755 | 10/1985 | Hagen et al. | 564/413 X |
| 4,711,964 | 12/1987 | Tan et al. | 548/461 |
| 4,783,514 | 11/1988 | Kirchhoff et al. | 526/281 |
| 4,822,930 | 4/1989 | Liu | 570/206 |

OTHER PUBLICATIONS

Polymer Reprints, vol. 27(2), 1986, pp. 240–241, Tan et al., Benzocyclobutene-maleimide Terminated Aromatic Imide AB-Monomers.
Tetrahedron, 21 (1965), pp. 245–254, Lloyd et al., The Electrophilic Substitution of Benzocyclobutene.
Synthesis, (1981) pp. 472–473, Sato et al., Condensation of Halobenzyenes and Haloferrocenes with Phthalimide in the Presence of Opper (1) Oxide; A simplified Gabriel Reaction.
Unit Processes in Organic Synthesis, McGraw Hill (5th ed., 1958), pp. 458, Groggins amination by ammonolysis.
Organic Synthesis, Coll., 3, John Wiley, New York (1955), pp. 307–309.
J. Chem. Soc. Perkin, 1 (1973), pp. 272–278, Bacon et al., Metal Ions and Complexes in Organic Reactions.
J. Amer. Chem. Soc. 42, (1920), pp. 1033–1042, J. A. Quick, The preparation of p-Phenylenediamine and Aniline from their Corresponding Chlorobenzenes.
Chem. Ber., 36 (1903), pp. 2382–2384, Ullmann.
Zh. Vses. Khim. Ova., 21, (1976), pp. 2274–2279, Shein et al.
Adv. Org. Chem., Wiley Interscience, (3rd. Edit. 1985) pp. 229–231, The effects of Structure on the Strengths of Acids and Bases.
J. Org. Chem., 40 (1975), pp. 3645–3650, Cohen et al., Copper(I)–Induced Reductive Dehalogenation, Hydrolysis or Coupling of Some Aryl and Vinyl Halides at Room Temperature.
Tetrahedron, 40, (1984), pp. 1433–1456, J. Lindley, Copper Assisted Nucleophilic Substitution of Aryl Halogen.
Horner, Chem. Ber., vol. 93 (1960), p. 1774.

*Primary Examiner*—Richard L. Raymond
*Attorney, Agent, or Firm*—Charlotte M. Kraebel; Charles J. Enright

[57] ABSTRACT

A process for preparing a 3- or 4-aminobenzocyclobutene comprises aminating a 3- or 4-halo- or sulfonyloxybenzocyclobutene reactant with an aminating agent by heating at a temperature from about 80° C. to a temperature at which dimerization or oligomerization of a benzocyclobutene reactant or product is a significant side reaction, in the presence of a metal-containing catalyst, for a time sufficient to aminate the halo- or sulfonyloxybenzocyclobutene reactant. In another aspect, this invention relates to a process for making a 3- or 4-phthalimido- or maleimidobenzocyclobutene, comprising reacting a 3- or 4-halobenzocyclobutene reactant with a phthalimide or maleimide compound in the presence of a metal-containing catalyst. The resulting phthalimido- or maleimidobenzocyclobutene can be hydrolyzed to a 3- or 4-aminobenzocyclobutene.

19 Claims, No Drawings

PROCESS FOR PREPARING AMINOBENZOCYCLOBUTENES

TECHNICAL FIELD

This invention relates to low temperature processes for preparing aminobenzocyclobutenes, which are useful as intermediates for specialty polymers. A low temperature process for preparing these intermediates is highly important, because benzocyclobutenes tend to polymerize through ring opening to orthoxylylene moieties at high temperatures. Accordingly, it is very desirable to provide a method for avoiding premature oligomerization or polymerization of benzocyclobutene compounds at high reaction temperatures, heretofore required for the preparation of aminobenzocyclobutenes.

BACKGROUND ART

The copper-catalyzed reaction of aromatic halides with amines or ammonium hydroxide is known.

Sato et al., *Synthesis*, (1981), pages 472-473, have recited reaction between iodobenzene and phthalimide, in the presence of copper (I) oxide in refluxing collidine.

Groggins, "Unit Processes in Organic Synthesis," McGraw-Hill (5th ed, 1958), has analyzed the ammonolysis of chlorobenzene by ammonium hydroxide in the presence of cuprous oxide. As shown in FIGS. 8-18, on page 458, amination of chlorobenzene is very slow at 160° C. Satisfactory rates for conversion of chlorobenzene to aniline are observed at 200°-210° C.

Nishiyama et al., in U.S. Pat. No. 4,380,670, have proposed converting 3,5-diaminochlorobenzene to 1,3,5-triaminobenzene with aqueous ammonium hydroxide, in the presence of cuprous chloride catalyst, preferably at 160°-190° C.

Conversion of 4-bromo-o-xylene to 3,4-dimethylaniline has been accomplished by reaction with ammonium hydroxide in the presence of cuprous chloride and copper at 195° C. This conversion is reported in *Organic Syntheses*, Coll. Vol 3, John Wiley, New York (1955), pages 307-309.

Cheveney et al, in U.S. Pat. No. 3,865,876, have recited converting 3,3'-dichlorobenzidine to 3,3'-diaminobenzidine using cuprous chloride catalyst and reaction temperature of 225° C. or higher.

Hale et al. in U.S. Pat. No. Re. 17,280, have proposed converting aromatic halides, e.g. chlorobenzene, to amines using aqueous ammonia solution in the presence of cuprous chloride at 150°-250° C.

Tan et al., in U.S. Pat. No. 4,711,964, disclose preparation of phthalimidobenzocyclobutene derivatives from an aminobenzocyclobutene.

It is an object of this invention to provide low temperature processes for the preparation of aminobenzocyclobutene compounds so as to prevent premature oligomerization or polymerization of resulting aminobenzocyclobutene products.

DISCLOSURE OF THE INVENTION

In one aspect, this invention relates to a process for preparing a 3- or 4-aminobenzocyclobutene, comprising aminating a 3- or 4-halo- or sulfonyloxybenzocyclobutene reactant with an aminating agent by heating at a temperature from about 80° C. to a temperature at which dimerization or oligomerization of a benzocyclobutene reactant or product is a significant side reaction, in the presence of a metal-containing catalyst for a time sufficient to aminate the halo- or sulfonyloxybenzocyclobutene.

In another aspect, this invention relates to a process for making a 3- or 4-phthalimido- or maleimidobenzocyclobutene, comprising reacting a 3- or 4-halo benzocyclobutene with a phthalimide or maleimide compound in the presence of a metal-containing catalyst.

DETAILED DESCRIPTION OF THE INVENTION

"Benzocyclobutene," as used in the specification and claims, includes carbocyclic and heterocyclic arylcyclobutene (cyclobutarene) compounds, which consist of a cyclobutene ring fused to an aromatic carbocyclic or heterocyclic ring. Aromatic as used herein refers to carbocyclic or heterocyclic rings in which $4n+2$ delocalized pi electrons are contained in an orbital ring. This property is also known as resonance stabilization or delocalization.

Preferred carbocyclic aromatic moieties include benzene, naphthalene, phenanthrene, anthracene, a biaryl moiety or two or more aromatic radicals, bridged by alkylene or cycloalkylene moieties. More preferred carbocyclic aromatic radicals include benzene, naphthalene, biphenyl, binaphthyl, diphenylalkane or diphenylcycloalkane radicals. The most preferred carbocyclic aromatic radical is a benzene radical, which, when fused to a cyclobutene ring, produces the simplest member of the series, benzocyclobutene.

Examples of preferred heterocyclic aromatic compounds include pyrrole, furan, thiophene, imidazole, oxazole, thiazole, pyrazine, pyridine and pyrimidine. More preferred heterocyclic aromatic radicals are pyridine, furan and thiophene, with cyclobutapyridine being most preferred. The carbocyclic analogs are preferred over the heterocyclic analogs.

Either the aryl radical or the cyclobutene ring can be substituted by electron-donating or electron-withdrawing groups. Examples of such substituents include cyano, halo, carboxy, hydrocarbyloxy, carbonyl, alkanoyl, aroyl, alkylsulfonyl, alkylsulfonoyl, amido, alkyl, alkenyl or aryl groups.

It will be understood that "benzocyclobutene" is an art-recognized term. In the commonly-used non-systematic numbering system for benzocyclobutenes, the 1- and 2-positions are in the cyclobutene ring. The 3- and 6-positions are in an aromatic ring, adjacent to the cyclobutene ring. The 4- and 5-positions are meta to the cyclobutene ring. The simplest member of the series, benzocyclobutene, is formally identified as bicyclo[4.2.0]octa-1,3,5-triene. A compound, formally identified as 3-bromobicyclo[4.2.0]octa-1,3,5-triene, is commonly known as 4-bromobenzocyclobutene. The common names will be used in the specification and claims.

The aminobenzocyclobutene products of this invention can be used for the preparation of bridged benzocyclobutenes of the formula

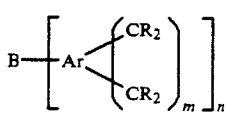

wherein B is an n-valent bridging moiety containing nitrogen, bonded to the aromatic ring (Ar) of the benzocyclobutene unit, m is an integer of 1 or more, n is an integer of 2 or more and each R is hydrogen or an electron-donating or electron-withdrawing substituent.

The aminobenzocyclobutene products of this invention can also be used to prepare derivatives of unbridged aminobenzocyclobutenes, for example, 3- or 4-(N-alkyl or N-alkanoyl)aminobenzocyclobutenes.

In the simplest cases, the cyclobutene ring is unsubstituted (each R is H and m is 1) and the aromatic ring is benzene. This case can be represented by the subgeneric formula

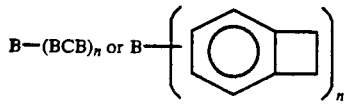

wherein B is the nitrogen-containing bridging function and n is as above. In this formula, BCB represents 3-or 4-benzocyclobutenyl.

Examples of nitrogen-containing bridging groups include, but are not limited to,

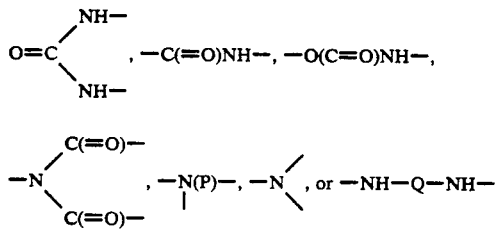

wherein P is H, alkyl or aryl and Q is a divalent bridging groups, such as phenylene, xylylene, alpha, omega-alkylene and the like. A preferred type of bridging group is that wherein Q is alkylene and the simplest products correspond to the general formula

in which x is an integer from 2-20. Most preferred of these bridging groups include those derived by reaction with 1,4-diaminobutane (tetramethylene diamine) or 1,6-diaminohexane (hexamethylene diamine).

Corresponding oxaalkylene diamines can be used as bridging groups. For example, B can be —NHC$_{x/2}$H$_x$-OC$_{x/2}$H$_x$NH—, wherein x is as above. Other nitrogen-containing bridging groups are disclosed by Kirchhoff et al., U.S. Pat. No. 4,540,763, herein incorporated by reference.

More preferred bridging groups include aromatic moieties, such as phenylene, tolylene, xylylene, naphthylenylene and the like, represented by the symbol AR, wherein AR is the residue of an aromatic moiety having n amino groups. The bridged products, containing unsubstituted BCB functionality can therefore be represented by the following typical formulas:

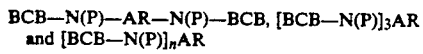

That is, AR is the residue of 1,2-diaminobenzene, 1,3-diaminobenzene, 1,4-diaminobenzene, 1,3,5-triaminobenzene, 1,2,4,5-tetraaminobenzene, 1,4,5,8-tetraaminonaphthalene, 1,5-diaminonaphthalene, 1,4-diaminonaphthalene, diaminoanthracene, triaminoanthracene, diaminophenanthrene, triaminophenanthrene and the like.

Exemplary unbridged benzocyclobutene compounds which can be aminated in accordance with this invention include, but are limited to, compounds of the structures:

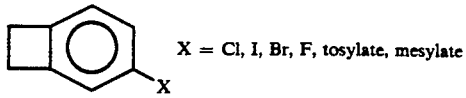

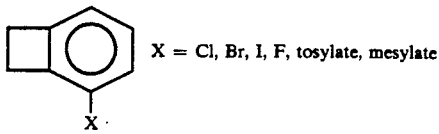

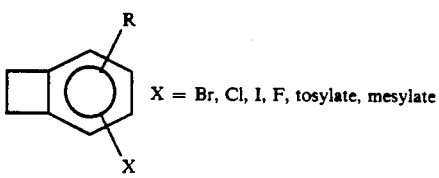

wherein R is alkyl, vinyl, substituted vinyl, ethynyl, substituted ethynyl, aryl, polyaryl, substituted aryl, substituted polyaryl, heterocyclic, heteroaryl, alkylaryl, alkylheterocyclic, arylheteroaryl, trialkylsilyl, nitro, cyanato, formyl, aroyl, alkanoyl, benzobicyclobutenyl, benzocyclobutenoyl, alkylbenzocyclobutenyl, arylbenzocyclobutenyl, alkylarylbenzocyclobutenyl, arylalkylbenzocyclobutenyl, oxybenzocyclobutenyl, thiobenzocyclobutenyl, benzocyclobutenyl sulfonyl, benzocyclobutenyl sulfoxide, carboxy, carbalkoxy, mono or dialkylamino, mono or diarylamino, mono or diheterocyclic amino, mono or diheteroaryl amino, hydroxy, alkoxy aryloxy, substituted alkoxy, substituted aryloxy, polyaryloxy, substituted polyaryloxy, mercapto, alkylthio, substituted alkylthio, arylthio, substituted arylthio, arylsulfoxyl, arylsulfoxide, polyarylthio, substituted polyarylthio, heterocyclothio and heteroarylthio. Substituted compounds include hydrocarbyl substituents, as recited by Kirchhoff, supra.

Representative higher fused ring benzocyclobutene reactants include, but are not limited to, compounds of the formulas:

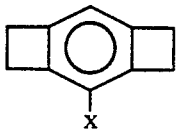

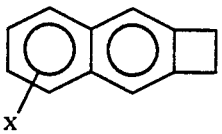

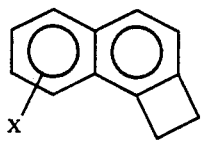

-continued

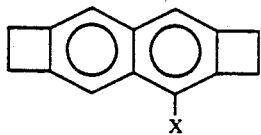
X

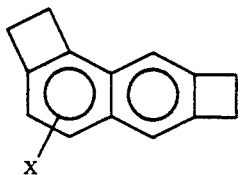
X

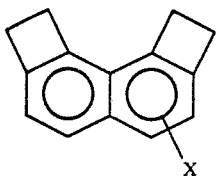
X

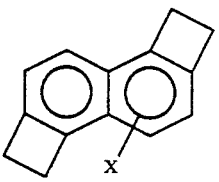
X

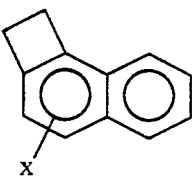
X

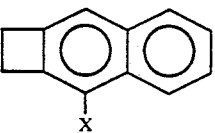
X

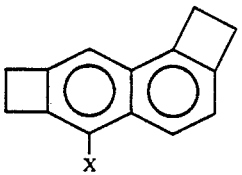
X wherein X is Cl, Br or I.

It will be understood that the fused ring benzocyclobutenes can be substituted as above and that dihalo fused ring benzocyclobutenes can also be used.

Preferred reactants for the practice of this invention are those containing a 3- or 4-halobenzocyclobutene moiety, more preferably a 4-halobenzocyclobutene moiety. Preferred halobenzocyclobutenes include the bromo, chloro and iodo compounds. The most preferred benzocyclobutene reactant is 4-bromobenzocyclobutene.

Monobrominated cyclobutarenes, particularly 4-bromobenzocyclobutene, can be prepared as recited by Liu, U.S. Pat. No. 4,822,930 herein incorporated by reference.

Hydroxybenzocyclobutenes are known compounds. A representative synthesis is reported by Horner, Chem. Ber., volume 93 (1960), page 1774. The hydroxy compounds can be converted to corresponding sulfonate esters by reaction with a sulfonyl halide, for example, toluenesulfonyl chloride, benzenesulfonyl chloride or methanesulfonyl chloride in the presence of a tertiary amine, which acts as a hydrogen halide acceptor.

The metal-containing catalyst can be selected from heavy metals or their compounds, including but not limited to elemental iron or copper, as well as compounds of copper (I), copper (II), iron (II), iron (III), silver (I), nickel (II), nickel(III), Zinc (II), palladium (0), palladium (II), sodium (I), potassium (I), calcium (II), magnesium (II), rhodium (II), rhodium (III), rhodium (IV), ruthenium (II), aluminum (III), antimony (III), antimony (V), titanium (IV), mercury (II) or lithium (I).

Preferred metal-containing catalysts are copper or copper (I) compounds. Representative copper (I) compounds include, but are not limited to the cyanide, iodide, sulfate, acetate, benzoate, bromide, chloride, isopropenylacetylide, nitride, phenylacetylide, thiocyanate or triflate. Copper includes copper metal, whether in the form of dust, wire or mesh, as well as copper bronze. Copper (I) compounds also include products, obtained by disproportionation of copper metal or another reducing agent, with copper (II) compounds. This reaction can be represented by the equation:

$$CuX_2 + Cu^o \rightleftharpoons 2\ CuX$$

wherein $X = Cl$, $Br$, $I$ or $\frac{1}{2}\ O$.

Particularly, preferred copper-containing catalysts include cuprous oxide and cuprous halides. Most preferred are cuprous chloride and cuprous oxide.

Aminating agents include, but are not limited to, ammonium hydroxide, liquid ammonia, methylamine, dimethylamine, ethylamine, n-butylamine, aniline, N-methylaniline, gaseous ammonia, ammonium hydroxide, sodium amide, potassium amide, sodium azide, potassium azide, copper azide, hydroxylamine, hydrazine, tertbutyl amine, hexamethylene diamine and tetramethylene diamine. Preferred aminating agents include lower alkylamines, e.g. methylamine or ethylamine, and ammonium hydroxide. A most preferred aminating agent is ammonium hydroxide.

The process of this invention can be run in any polar solvent, in which a nucleophilic reaction can occur. These include N,N-dimethylformamide, dimethyl sulfoxide, N-methylpyrrolidinone, pyridine, collidine, lutidine, and water. In cases in which a halo- or sulfonyloxybenzocyclobutene reactant is being converted to an unsubstituted amine, it is preferred to use water as the solvent, generally providing the water in the aqueous ammonium hydroxide solution used as the aminating agent.

The process of this invention can be carried out in any container, with or without a stirring attachment, which can be heated to the required temperature, which can withstand pressures of 3-75 atm and which is not attacked by the reactants, catalysts or products of the invention.

The molar ratio of benzocyclobutene reactant to aminating agent is from about 1:2 to about 1:1000. The preferred range is from about 1:2 to about 1:50, most preferably from about 1:2 to about 1:20.

The molar ratio of benzocyclobutene reactant to metal-containing catalyst is from about 500:1 to about 1:1. Preferably, the ratio is from about 100:1 to 1:1, most preferably from about 50:1 to about 1:1.

The temperature for performing the process of this invention is from about 80° C. to a temperature at which dimerization or oligomerization of the benzocyclobutene reactant or product becomes a significant side reaction. The upper temperature limit can be determined empirically, by known methods, such as following the progress of the reaction using gas chromatography. It has been found that appreciable dimerization or oligomerization occurs at temperatures above 200° C., or even above 180° C. Therefore, it is preferred to carry out the process of this invention from about 100° C. to about 180° C. More preferably, the reaction is carried out from 120° C. to about 160° C., most preferably, from about 140° C. to about 160° C.

The pressure, at which the process is carried out, will depend upon the aminating agent selected. For aminations, carried out with ammonia or ammonium hydroxide, the reactions will preferably be done at elevated pressures, which are determined by the temperature to which the reaction mixture is heated. When aminating agents, which are liquids at high temperatures and which do not have high vapor pressures under reactions conditions, are used, the reactions may be done at atmospheric pressure or slightly elevated pressures.

The process of converting halobenzocyclobutenes or sulfonyloxybenzocyclobutenes to aminobenzocyclobutenes in a direct one-step amination, catalyzed by a metal-containing compound, is particularly advantageous because the low reaction temperature results in a very low degree of oligomerization or polymerization. The products of the one-step reaction can be purified, by a combination of extraction and distillation, to a purity above 95%.

It has also been found that the volume of reactants in a closed reactor significantly affects the outcome of the reaction. It is preferred that at least 50% of the reactor volume be occupied by the reactants. Most preferably, the reactor volume is at least ⅔ full with liquid reactants.

An alternative process is that wherein a 3- or 4- halobenzocyclobutene reactant is treated with a phthalimide or maleimide to produce a 3- or 4-phthalimido-or maleimidobenzocyclobutene. When phthalimide or maleimide is monomeric, for example, phthalide or maleimide themselves, the product can be cleaved by reaction with an amine to produce a corresponding aminobenzocyclobutene. A preferred amine for this purpose is hydrazine, preferably hydrazine hydrate.

When the phthalimide is bridged, bisdienes of the types disclosed by Tan et al., U.S. Pat. No. 4,711,964 can be obtained in one step, rather than by a process of reacting an aminocyclobutene with a dianhydride or polyanhydride. Bridging functions, contemplated for this purpose include those, disclosed by Tan et al., herein incorporated by reference. The resulting bisdienes can be reacted with mononenes or bisdienophiles in a variety of Diels-Alder condensations, as disclosed by Tan et al.

In this process, a most preferred reactant is a bisphthalimide. Another particularly preferred reactant is bis-(2,2-phthalimido)hexafluoropropane.

The metal-containing catalyst can be selected from those disclosed above. The preferred catalyst is copper or a copper (I) compound, most preferably cuprous oxide. The reaction temperature is in the ranges, recited above, with temperatures of 140°–180° C. being most preferred.

Cyclobutapyridines can be prepared by the pyrolysis of 4-pyridyl propargyl ether at 550° C. See J. M. Riemann et al., *Tetrahedron Letters*, no. 22 (1977), pages 1867–1870. Alternatively, a pyridine-4-carbonitrile, having an alkyl substituent on the carbon atom adjacent to the nitrile, is reacted with sodium azide and ammonium chloride in N,N-dimethylformamide to prepare a 5-(alkyl-4-pyridyl)tetrazole. The 5-(alkyl-4-pyridyl)tetrazole is pyrolyzed at about 600° C. to a cyclobutapyridine. See W. D. Crow et al., Australian Journal of Chemistry (1975), after page 1741. 2-Bromocyclobuta[b]pyridine can be prepared from 2-hydroxy[b-]cyclobutapyridine. See Kirchhoff et al., U.S. Pat. No. 4,783,541, herein incorporated by reference.

BEST MODE FOR CARRYING OUT THE INVENTION

In a most preferred embodiment, the process of this invention is that wherein the benzocyclobutene reactant is a 3- or 4-halobenzocyclobutene, the metal-containing catalyst is cuprous oxide, the reaction is carried out at a temperature from about 140° C. to about 160° C. and the aminating agent is ammonium hydroxide.

Without further elaboration it is believed that one skilled in the art can, using the preceding description, utilize the present invention to its fullest extent. The following preferred specific embodiments are, therefor, to be construed as merely illustrative and not limitative of the remainder of the disclosure in any way whatsoever.

In the following examples, the temperature are set forth uncorrected in degrees Celsius. Unless otherwise indicated, all parts and percentages are by weight.

EXAMPLE 1

Ammonolysis of 4-Bromobenzocyclobutene

To a 50-mL 316 stainless steel Parr reactor, equipped with a stirrer, thermocouple, sampling tube and rupture disk set for 136.0 atm pressure, is charged 5.0 g (27.32 mmol) of 4-bromobenzocyclobutene, 30 mL of aqueous 28% ammonium hydroxide (7.56 mL, 216 mmol) and 0.24 g (1.68 mmol) of cuprous oxide. The reactor is closed and placed in a heating mantle, after which the overhead stirrer coupling is engaged.

The reactor is heated to 150° C. with vigorous stirring and maintained at 150° C. for 4 hours. During this time, the pressure in the reactor reaches 18.7 atm. At the end of 4 hours, heating is stopped. The reactor is cooled to room temperature and excess pressure is relieved by opening a vent valve.

The reactor is opened and a two-phase reaction mixture is removed and transferred to a separatory funnel. Methylene chloride (50–100 mL) is added to the mixture, which is shaken. The resulting organic phase is removed and the aqeous layer is extracted with a 150-mL portion of methylene chloride. The combined methylene chloride layers are dried over magnesium sulfage and then filtered through diatomaceous earth. After removing the volatiles in vacuo, there is obtained 3.20 g of a liquid product.

The crude product contains less than 2% of 4-bromobenzocyclobutene and 92.2% of 4-aminobenzocyclobutene (capillary gas chromatography). Minor impurities, as well as 2-3% of higher molecular components, are present.

The crude product is distilled by bulb to bulb distillation in vacuo to give 2.87 g of water white product, wt 2.87 g (88%), b 95°-105° C./6 mm Hg.

The product is more than 95% pure (gas chromatography). Mass spectrometry indicates that the parent ion (m/e) is 119. H— and C—NMR are consistent with the proposed structure of the product.

EXAMPLE 2

(a) Reaction of 4-Bromobenzocyclobutene with Phthalimide

4-Bromobenzocyclobutene (1.0 g 5.46 mmol), phthalimide (0.064 g, 6.552 mmol), cuprous oxide (0.469 g, 3.28 mmol) and 15 mL of 4-picolie are charged to a 50-mL round-bottom flask, fitted out with a reflux condenser, thermometer well and magnetic stirrer. The mixture is heated at 145° C. for 18 hours. The yield of 4-(N-phthalimido)benzocyclobutene is 64%, crystalline solid, mp 177.2° C.

(b) Hydrolysis of Phthalimide with Hydrazine Hydrate

The phthalimide is hydrolyzed by heating with hydrazine hydrate (1:1 mole ratio) in ethanol at 78° C. for 0.5 hours. The yield of 4-aminobenzocyclobutene is 80%. The overall yield is 51%.

(c) Preparation of 4-Aminobenzocyclobutene from 4-Mesyloxybenzocyclobutene

4-Mesyloxybenzocyclobutene is prepared by reaction between 4-hydroxybenzocyclobutene and mesyl chloride (methanesulfonyl chloride) in pyridine, using excess pyridine as solvent. The mesyloxy compound is reacted with maleimide, otherwise as in paragraph (a), to produce 4-(N-maleimidyl)benzocyclobutene, which is hydrolyzed with hydrazine hydrate to 4-aminobenzocyclobutene, otherwise as in paragraph (b).

(d) Reaction of 4-Iodobenzocyclobutene with Bis-(2,2-phthalimido)-hexafluoropropane 4-Iodobenzocyclobutene and bis-(2,2-phthalimido)-hexafluoropropane are reacted, otherwise as in paragraph (a), to produce a corresponding bis-(4-benzocyclobutenyl) derivative.

(e) Hydrolysis of Intermediate Phthalimide with 1,4-Diaminobutane

The phthalimide of (a) is hydrolyzed with a five-fold excess of 1,4-diaminobutane as in (b). The product is a mixture of 4-(4-N-butylamino)benzocyclobutene and 1,4-bis[N-(4-benzocyclobutenyl)amino]butane.

TABLE 1

| Temp. (°C.) | Time (h) | Amino-BCB[a] GC area | Isolated | High mw[c] | Br-BCB[b] |
|---|---|---|---|---|---|
| 200[d] | 4 | 5% | 5.9% | 48% | 20% |
| 180[d] | 4 | 35% | 34.6 | 18.7 | 41 |
| 180[e] | 4 | 47.6 | 40 | 36.6 | 3.0 |
| 180[e] | 2 | 64.3 | 52 | 23.9 | 5.3 |
| 180[e] | 1 | 54.7 | 61 | 5.9 | 35 |
| 160[e] | 4 | 82.4 | 88 | 13.8 | 1.5 |
| 150[e] | 4 | 93 | 93 | 1.8 | 1.0 |
| 140[e] | 4 | 92.3 | | 0.9 | 2.2 |
| 140[e] | 2 | 44.1 | | <0.5 | 48.8 |
| 120[e] | 4 | 48.4 | | <0.5 | 46.9 |

TABLE 1-continued

| Temp. (°C.) | Time (h) | Amino-BCB[a] GC area | Isolated | High mw[c] | Br-BCB[b] |
|---|---|---|---|---|---|
| 100[e] | 4 | 4.8 | | <0.5 | 91.5 |

[a]Amino-BCB = 4-aminobenzocyclobutene
[b]Br-BCB = 4-bromobenzocyclobutene
[c]High mw = oligomers of amino-BCB or Br-BCB
[d]Runs in 50-mL pressure vessel, charged with 54.9 mmol of 4-Br-BCB, 180 mmol of ammonium hydroxide and 0.8 mmol of cuprous oxide
[e]Runs in 50-mL pressure vessel, charged with 27.5 mmol of 4-Br-BCB, 216 mmol of ammonium hydroxide and 1.6 mol of cuprous oxide

(f) Hydrolysis of Intermediate Phthalimide with 1,4-Diaminobenzene

The phthalimide of (a) is hydrolyzed with a five-fold excess of 1,4-diaminobenzene as in (b). The product is a mixture of 4-(N-phenylamino)benzocyclobutene and 1,4-bis[N-(4-benzocyclobutenyl)amino]benzene.

EXAMPLE 3

Effect of Reaction Temperatures and Reactant Volume on Product Distribution from Ammonolysis of 4-Bromobenzocyclobutene Reactions are run using the following charges:
54.9 mmol of 4-bromobenzocyclobutene, 180 mmol of ammonium hydroxide and 0.8 mmol of cuprous oxide; reactant volume about 28 mL or
27.5 mmol of 4-bromobenzocyclobutene, 216 mmol of ammonium hydroxide and 1.6 mmol of cuprous oxide; reactant volume about 35 mL. Results for runs at temperatures from 100° C. to 200° C. are given in Table 1.

It is apparent from Table 1 that significant amounts of higher molecular weight products, including dimers or oligomers of bromo- or amino-benzocyclobutene, are obtained at 180° C. or higher. The production of higher molecular weight products at 180° C. can be decreased by using a lesser volume of reactants (second and third runs in the Table). This is accomplished with a corresponding decrease in conversion to aminobenzocyclobutene.

Analysis of the data in Table 1 shows that optimum conversions to amino-BCB are realized at 140°-160° C.

EXAMPLE 4

(a) Ammonolysis of 4-Bromobenzocyclobutene Using Cuprous Oxide at 200° C.

To a 50-mL Parr pressure reactor is charged 1.0 g (5.46 mmol) of 4-bromobenzocyclobutene, 14 mL of 28% aqueous ammonium hydroxide (109.3 mmol) and 156 mg (1.092 mmol) of cuprous oxide. The reactor is sealed and stirred and heated to 200° C. and maintained at 200° C. for 4 hours.

The reactor is cooled to room temperature and vented to relieve pressure built up. The reaction mixture is worked up as in Example 1. The product comprises 25% of 4-aminobenzocyclobutene and 61.2% of 4-bromobenzocyclobutene (GC).

This experiment shows that use of a very large excess of ammonium hydroxide increases conversion to aminobenzocyclobutene under conditions, otherwise the same as in the first run on Table 1.

(b) Ammonolysis of 4-Bromobenzocyclobutene in the Presence of Cuprous Chloride

A reaction is run, as in (a), using as catalyst cuprous chloride (108 mg, 1.092 mmol). The product contains 9% of 4-aminobenzocyclobutene, 58% of 4-bromobenzocyclobutene and 10.2% of higher molecular weight material (GC).

(c) Scaled Up Reactions

Reaction similar to those disclosed in Example 3 are carried out in a two liter reactor. Changing the ratio of 4-bromobenzocyclobutene to ammonium hydroxide from 1:7.85 to 1:5.6 at 140°–160° C. reaction temperature produces similar product mixtures.

EXAMPLE 5

(a) Aminolysis of 4-Bromobenzocyclobutene with Methylamine

4-Bromobenzocyclobutene (40.0 g, 0.2185 mol), methylamine (100 g of 40% solution, 1.29 mol) and cuprous oxide (1.56 g, 0.0109 mol) are charged to a 250-mL Fluitron reactor. The reactor is sealed and purged four times with nitrogen (6.8 atm, gauge). The contents of the reactor are stirred at 1100 rpm and heated to 140° C. and maintained at 140° C. for 16.5 hours.

The reactor is cooled to room temperature and opened. A sample, subjected to GC analysis, contains no Br-BCB, 56.5% of 4-methylamino-BCB and about 11% of heavies.

The reaction mixture is transferred to a 250-mL separatory funnel and diluted with 250 mL of methylene chloride. After the mixture is shaken, the layers are allowed to separate and the bottom layer is removed. The upper layer is extracted with 75 mL of methylene chloride. The organic layers are combined and the upper aqueous layer is discarded.

The organic layer is washed with two 20-mL portions of distilled water and filtered over a mixture of 15 g of silica gel and 10.0 g of magnesium sulfate. Methylene chloride is removed from the filtrate using a rotary evaporator. The crude product contains 4.2% of volatiles, no Br-BCB, 92.7% of 4-methylamino-BCB and about 2.0% of heavies (GC).

(b) Aminolysis of 4-Bromobenzocyclobutene with n-Butylamine

4-Bromobenzocyclobutene (40.0 g, 0.2186 mol), n-butylamine (126 g, 1.726 mol) and cuprous oxide (1.68 g, 0.01145 mol) are charged to the Fluitron reactor. The reactor is purged as in (a) and heated at 140°–150° C. Samples are removed at intervals and analyzed by GC.

The mixture, after 32.5 hours heating contains 52.25% of unreacted 4-BrBCB and 35.03% of 4-butylamino-BCB. At the end of 165 hours heating, the mixture contains 56.62% of 4-butylamino-BCB, 7.98% of 4-Br-BCB and 14.07% of unidentified products.

EXAMPLE 6

(a) Ammonolysis of 4-Iodobenzocyclobutene; Cuprous Oxide

An experiment is run, otherwise as in Example 1, using 4-iodobenzocyclobutene instead of 4-bromobenzocyclobutene. Similar results are obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for preparing a 3- or 4-aminobenzocyclobutene, comprising aminating a 3- or 4- halo- or sulfonyloxybenzocyclobutene reactant with an aminating agent by heating at a temperature from about 140° C. to about 160° C., in the presence of a metal-containing catalyst for a time sufficient to aminate the halo- or sulfonyloxybenzocyclobutene.

2. The process of claim 1, wherein the benzocyclobutene reactant is a 3- or 4-halobenzocyclobutene.

3. The process of claim 1, wherein the benzocyclobutene reactant is 4-bromobenzocyclobutene.

4. The process of claim 1, wherein the metal-containing catalyst is copper oxide, copper hydroxide or a copper salt.

5. The process of claim 1, wherein the metal-containing catalyst is cuprous oxide.

6. The process of claim 1, wherein the aminating agent is ammonium hydroxide.

7. The process of claim 1, wherein the aminating agent is a lower alkylamine.

8. The process of claim 1, wherein the ratio of aminating agent to benzocyclobutene starting compound is from about 2:1 to about 50:1.

9. The process of claim 1, wherein the ratio of aminating agent to benzocyclobutene starting compound is from about 2:1 to about 20:1.

10. The process of claim 1, wherein the benzocyclobutene reactant is a 3- or 4-halobenzocyclobutene, the metal-containing catalyst is cuprous oxide, and the aminating agent is ammonium hydroxide.

11. The process of claim 10, wherein the benzocyclobutene reactant is 4-bromobenzocyclobutene.

12. The process of claim 6, carried out in a closed reactor, wherein the volume of reactants occupies more than about 50% of the reactor volume.

13. The process of claim 10, carried out in a closed reactor, wherein the volume of reactants occupies more than about 50% of the reactor volume.

14. The process of claim 1, comprising reacting a 3- or 4-halobenzocyclobutene with an aminating agent selected from the group consisting of a phthalimide or maleimide compound to produce a 3- or 4-phthalimido- or maleimidobenzocyclobutene.

15. The process of claim 14, wherein the metal-containing catalyst is cuprous oxide.

16. The process of claim 14, wherein the halobenzocyclobutene is 4-bromobenzocyclobutene.

17. The process of claim 14, wherein the phthalimide compound is phthalimide.

18. The process of claim 14, including the further step of cleaving the thus-formed benzocyclobutenylphthalimide or -maleimide with hydrazine to produce a corresponding aminobenzocyclobutene.

19. The process of claim 14, wherein the phthalimide is bis-(2,2-phthalimido)hexafluoropropane.

* * * * *